US010571399B2

(12) United States Patent
Barcelo et al.

(10) Patent No.: US 10,571,399 B2
(45) Date of Patent: Feb. 25, 2020

(54) ANALYTE DETECTION PACKAGE HOUSING

(71) Applicant: Hewlett-Packard Development Company, L.P., Houston, TX (US)

(72) Inventors: Steven Barcelo, Palo Alto, CA (US); Ning Ge, Palo Alto, CA (US); Kevin Dooley, Leixlip (IE); Zhiyong Li, Palo Alto, CA (US)

(73) Assignee: Hewlett-Packard Development Company, L.P., Spring, TX (US)

( * ) Notice: Subject to any disclaimer, the term of this patent is extended or adjusted under 35 U.S.C. 154(b) by 240 days.

(21) Appl. No.: 15/570,363

(22) PCT Filed: Jul. 29, 2015

(86) PCT No.: PCT/US2015/042652
§ 371 (c)(1),
(2) Date: Oct. 30, 2017

(87) PCT Pub. No.: WO2017/019060
PCT Pub. Date: Feb. 2, 2017

(65) Prior Publication Data
US 2018/0143135 A1 May 24, 2018

(51) Int. Cl.
*G01N 21/64* (2006.01)
*G01N 21/65* (2006.01)
(52) U.S. Cl.
CPC ......... *G01N 21/645* (2013.01); *G01N 21/658* (2013.01); *G01N 2021/6482* (2013.01); *G01N 2021/651* (2013.01)

(58) Field of Classification Search
CPC .............. G01N 21/645; G01N 21/658; G01N 2021/6482; G01N 2021/651; G01N 21/648
See application file for complete search history.

(56) References Cited

U.S. PATENT DOCUMENTS 8,593,629 B2 11/2013 Santori et al.
2009/0296218 A1 12/2009 Ryytty
(Continued)

FOREIGN PATENT DOCUMENTS

CN 203574634 4/2014
CN 103797352 5/2014
(Continued)

OTHER PUBLICATIONS

Angelis, F.D. et al., Breaking the diffusion limit with super-hydrophobic delivery of molecules to plasmonic nanofocusing SERS structures, (Web Page), Jun. 9, 2011.
(Continued)

*Primary Examiner* — David P Porta
*Assistant Examiner* — Meenakshi S Sahu
(74) *Attorney, Agent, or Firm* — Rathe Lindenbaum LLP

(57) ABSTRACT

In one example, an analyte detection package includes a substrate, surface-enhanced luminescence (SEL) structures extending from the substrate and a low wettability housing. The SEL structures have a first wettability for a given liquid. The low wettability housing extends from the substrate to form a chamber between the housing of the substrate about the SEL structures to receive an analyte containing solution. The housing has an inner surface adjacent the chamber, wherein the inner surface has a second wettability for the given liquid less than the first wettability.

15 Claims, 4 Drawing Sheets

(56) References Cited

U.S. PATENT DOCUMENTS

| | | |
|---|---|---|
| 2010/0085565 A1 | 4/2010 | Koo et al. |
| 2010/0285573 A1 | 11/2010 | Leck et al. |
| 2012/0287427 A1 | 11/2012 | Li et al. |
| 2013/0171413 A1 | 7/2013 | Khan et al. |
| 2013/0171685 A1 | 7/2013 | Schutze et al. |
| 2014/0199235 A1 | 7/2014 | Jeong et al. |
| 2014/0339090 A1* | 11/2014 | Huang ................ B01L 3/50273 204/603 |
| 2014/0362373 A1 | 12/2014 | Lin et al. |
| 2015/0077746 A1 | 3/2015 | Li et al. |
| 2015/0126393 A1 | 5/2015 | Corn et al. |

FOREIGN PATENT DOCUMENTS

| | | |
|---|---|---|
| CN | 103822912 | 5/2014 |
| EP | 2196796 | 6/2010 |
| EP | 2693196 | 2/2014 |
| JP | 2014235115 | 12/2014 |
| TW | 201447276 A | 12/2014 |
| WO | WO-2009020479 | 2/2009 |
| WO | WO-2013158114 | 10/2013 |
| WO | WO-2014188237 | 11/2014 |

OTHER PUBLICATIONS

Yang, S. et al., Superhydrophobic Surface Enhanced Raman Scattering Sensing using Janus Particle Arrays Realized by Site-Specific Electrochemical Growth, (Research Paper) Jan. 21, 2014.

* cited by examiner

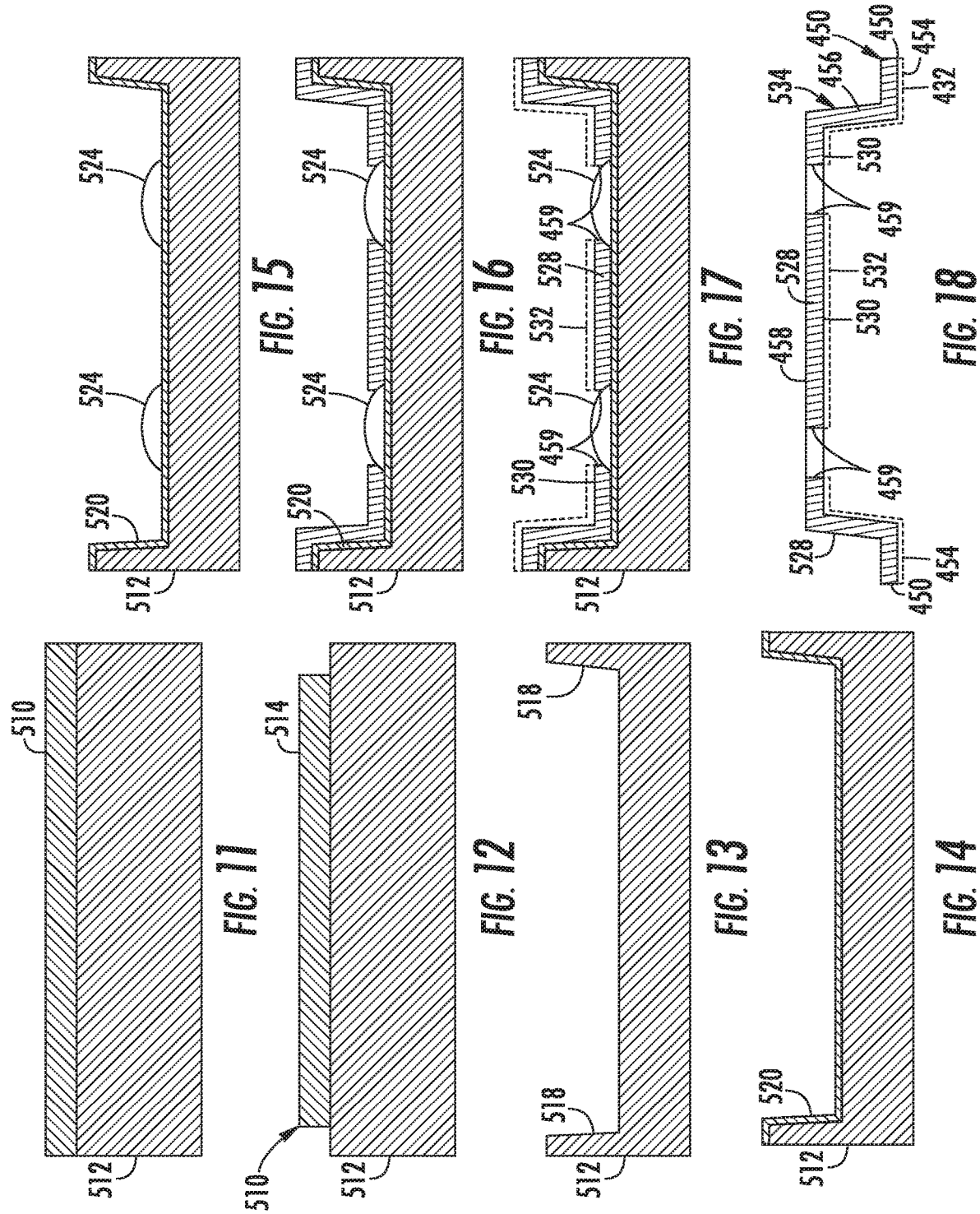

ANALYTE DETECTION PACKAGE HOUSING

BACKGROUND

Surface enhanced luminescence (SEL) is sometimes used for analyzing the structure of inorganic materials and complex organic molecules. SEL focuses electromagnetic radiation or light onto an analyte or solution containing an analyte, wherein the interaction between the light and the analyte is detected for analysis.

BRIEF DESCRIPTION OF THE DRAWINGS

FIGS. 11-18 are sectional views illustrating an example method or forming an example housing for being joined to a substrate with an SEL structure to form an analyte detection package.

DETAILED DESCRIPTION OF EXAMPLES

Figure 1:
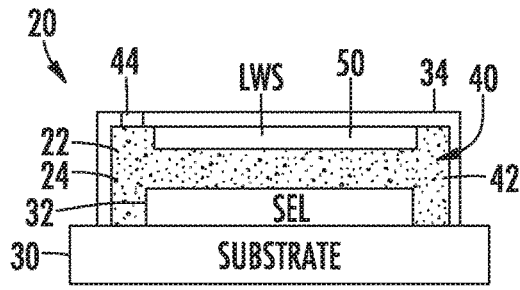
FIG. 1 is a sectional view schematically illustrating an example analyte detection package.

FIG. 1 schematically illustrates an example analyte detection package 20. Package 20 comprises a self-contained unit that is to receive and contain a solution 22 including an analyte 24 (schematically represented) for testing with a radiation source that directs light irradiation on the analyte 24 residing upon a surface enhanced luminescence (SEL) structure within the package. Radiation scattered or re-emitted by the analyte is detected and analyzed to identify the structure of inorganic materials and complex organic molecules. As will be described hereafter, package 20 concentrates the analyte 24 onto an SEL structure for enhanced sensing sensitivity by reducing absorption of solution 22 and analyte 24 on the walls of package housing.

Package 20 comprises a substrate 30, surface enhanced luminescence (SEL) structure 32 and housing 34. Substrate 30 cooperates with housing 34 to form an enclosure or chamber 40 that extends about SEL structure 32 and contains solution 22. Substrate 30 comprises a base or platform supporting SEL structure 32. In one implementation, substrate 30 comprises a silicon substrate. In one implementation, substrate 30 has an upper surface forming a floor of chamber 40, wherein the upper surface comprises a metal that enhances or intensifies luminescence to enhance SEL testing. In one implementation, substrate 30 has an upper surface formed from a metal such as gold, silver, palladium or rhodium.

SEL structure 32 comprises a structure that serves as a stage upon which analyte deposits, wherein the SEL structure 32 enhances the intensity of the radiation scattered or reemitted by the analyte. Structure 32 may enhance the amount of radiation or the number of photons that are scattered or re-emitted by the analyte upon being impinged by radiation from a radiation source. In one implementation, structure 32 comprises an SEL structure or a group of SEL structures within chamber 40 upon which and about analyte 24 contacts.

In one implementation, the SEL structures comprise enhanced fluorescence spectroscopy structures or surface enhanced Raman spectroscopy (SERS) structures. Such structures may include a metal surface or structure, wherein interactions between the analyte and the metal surface may cause an increase in the intensity of the Raman-scattered radiation. Such metal surfaces may include a roughened metal surface, such as periodic gratings. In another implementation, such metal surfaces may comprise assemble nanoparticles. In some implementations, such metal surfaces may comprise metal islands.

In one implementation, such metal islands comprise flexible columnar supports such as pillars, needles, fingers, particles or wires. In some implementations, the flexible columnar structures may include a metal cap or head upon which an analyte may be deposited. In some implementations, such columnar structures are formed from materials and/or are dimensioned so as to bend or flex towards and away from one another in response to applied electric fields. In some implementations, the SERS structures are movable and are self-actuating, wherein such columnar structures bend or flex towards one another in response to micro-capillary forces so as to self-organize, wherein such bending facilitates close spacing between the structures for greater scattered radiation intensity.

Housing 34, sometimes referred to as an orifice plate, cooperates with substrate 30 to form and define the interior 42 of chamber 40. Housing 34 may protect SEL structure 32 from exposure to the environment and reduces or prevents oxidation of surfaces of SEL structure 32 prior to use. Housing 34 may additionally reduce or even prevent unintentional or premature exposure of SEL structure 32 to extraneous substances or an analyte that SEL structure 32 is intended to detect. Although housing 34 and substrate 30 are illustrated as forming a rectangular shaped interior 42, in other implementations, chamber 40 may have other shapes.

As schematically shown by FIG. 1, housing 34 comprises fill opening 44 and low wetting surface 50. Fill opening 44 may comprise an opening extending through a wall of housing 34. Fill opening 44 may facilitate filling of interior 42 with solution 22 including analyte 24. In one implementation, the fill opening is closed by a removable seal that may be peeled away, punctured or torn to expose the fill opening. In one implementation, the opening is formed by peeling, puncturing or penetrating through a portion of the walls of chamber 40. In one implementation, portions of chamber 40 are formed from material and/or are dimensioned so as to be torn away or peeled away to form the fill opening. In another implementation, chamber 40 has a portion which is to be punctured. In yet another implementation, chamber 40 comprises a septum through which a needle is used to deposit solution 22 containing analyte 24 into the interior 42 of chamber 40.

Low wetting surface 50 comprises a surface having a low degree a wettability as measured with respect to the solution 22 to be contained within interior 42. Wetting or wettability may refer to the ability of a liquid to maintain contact with a solid surface, wherein the degree of wettability is based upon a force balance between adhesive and cohesive forces. Low wetting surface 50 has a wettability that is less than the wettability of SEL structure 32 with respect to ethanol. In other words, SEL structure 32 may have a first wettability while low wetting service 50 has a second wettability less than the first wettability of SEL structure 32. As a result, solution 22 and the suspended analyte 24 may be less likely to be adsorbed onto the low wetting surface 50 of housing 34 as compared to SEL structure 32. Consequently, the analyte may be more likely to be adsorbed onto SEL structure 32, providing enhanced sensing sensitivity.

Wettability may be defined by a wettability contact angle. A contact angle may refer to the angle at which a liquid-vapor interface meets the solid-liquid interface as a result of adhesive and cohesive forces. Surfaces having a contact angle greater than 90° with respect to a given liquid may have low wettability such that the surface will have reduced contact with the liquid which will have a tendency to form compact liquid droplet. Surfaces having a contact angle greater than 150° (sometimes referred to as superphobic or super hydrophobic with respect to water) may have almost no contact with a liquid drop. In one implementation, low wetting surface 50 has a wettability contact angle of greater than 90° as measured with ethanol. In one implementation, low wetting surface 50 has a wettability contact angle of greater than 110° as measured with ethanol. In yet another implementation, low wetting surface 50 has a wettability contact angle of greater than 150° as measured with ethanol. In other implementations, low wetting surface 50 has a wettability contact angle of at least 90°, nominally greater than 110° or even greater than 150° as measured with other solvents of solution 22, such as acetone or water. When measured with water, the low wettability nature of surface 50 may be described as hydrophobic.

Because low wetting surface 50 has a wettability contact angle of greater than 90°, as solution 22 is evaporated, the remaining solution 22 and suspended analyte 24 may be less likely to adsorb along the low wetting surface 50, instead subsequently adsorbing onto SEL structure 32. In other words, the liquid or solution 22 may preferentially concentrate away from the interior low wetting surface 50 of housing 34 and therefore on the surface of SEL structure 32 as it dries. The greater concentrations of analyte 24 subsequently adsorbed onto SEL structure 32 may lead to a greater interaction of such analyte molecules with SEL structure 32 to increase performance sensitivity when package 20 is used.

As schematically illustrated by FIG. 1, low wetting surface 50 extends along an interior face or surface of housing 34 adjacent interior 42 so as to directly contact solution 22 when interior 42 has been filled with solution 22. In one implementation, low wetting surface 50 extends across a majority of the internal surface of housing 34 adjacent interior 42. In one implementation, low wetting surface 50 extends across an upper surface or ceiling of housing 34. In one implementation, low wetting surface 50 extends along the interior side surfaces of housing 34. In one implementation, low wetting surface 50 extends over or along an entire interior surface or the entire surface area of housing 34 that extends adjacent to interior 42.

In one implementation, low wetting surface 50 is formed by engineering an internal surface of the wall forming housing 34. For example, in one implementation, the internal surface of the wall forming housing 34 may be roughened so as to achieve the above-described wettability contact angles. In one implementation, interior surface of housing 34 is roughened to a micro roughness of at least one micrometer and up to 100 µm. In another implementation, the micro roughness surface of housing 34 is further roughened to provide a secondary nanoscale roughness of at least 50 nm and up to 200 nm. In essence, the peaks and valleys of the nanoscale roughness areas extend along the peaks and valleys of the micro scale roughness areas. In one implementation, the roughening of the interior surface of the wall or walls of housing 34 to form low wetting surface 50 is produced by etching such interior surfaces, such as with an unpatterned laser, chemical or plasma etching. In other implementations, such roughening may be induced or carried out by photolithography, imprint lithography been performed on the wall of housing 34.

In other implementations, low wetting surface 50 may be provided on the inner surface of housing 34 by securing a low wettability layer to the inner surface of housing 34. For example, the low wettability layer may be bonded, coated, fused, fastened otherwise joined to the existing walls of housing 34. The low wettability layer that is secured to housing 34 may have a low wettability that is less than the wettability of SEL structure 32 or that has a wettability contact angle of at least 90° as measured with water due to the layer itself being roughened (as described above) or due to the material composition of the layer. For example, in one implementation, low wetting surface 50 may comprise a coating of a material having a material composition that provides low wettability or wettability contact angle of at least 90° as measured with ethanol. In one implementation, low wetting surface 50 may comprise a coating of a flourocarbon such as polytetrafluoroethylene, wherein the low wetting surface exhibits a wettability contact angle greater than 90° with respect to solvents such as acetone and water. In other implementations, the low wettability layer may be formed upon the wall using sole-gel deposition or chemical vapor deposition for growth of nano wires.

Figure 2:
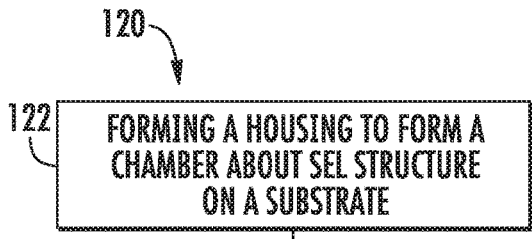
FIG. 2 is a flow diagram illustrating an example method for forming an analyte detection package.

FIG. 2 is a flow diagram of an example method 100 for forming an analyte detection package, such as the example analyte detection package 20. As indicated by block 102, a substrate, such as substrate 30, supporting a SEL structure or structures, such as SEL structure 32, is provided. As indicated by block 104, a low wettability housing, such as housing 34, is secured to the substrate to form a chamber, such a chamber 40, to contain an analyte containing solution about the SEL structure or structures. The low wettability housing has an inner surface with a wettability contact angle of greater than 90° relative to the solution or solvent to be contained about the SEL structures. In one implementation, the inner surface has a wettability contact angle of greater than 90° as measured with ethanol. In another implementation, inner surface has a wettability contact angle of greater than 90° as measured with other solvents such as acetone and water.

Figure 3:
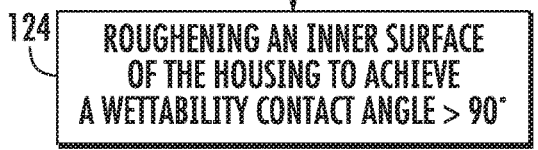
FIG. 3 is a flow diagram of an example method for forming a low wetting package housing.

FIG. 3 is a flow diagram of an example method 120 for forming a low wettability housing for use in method 100 or for use as part of package 20 described above. As indicated by block 122, a housing shaped and sized to form a chamber about an SEL structure on a substrate is formed. In one implementation, the housing may be formed using plating, molding or other fabrication technologies.

As indicated by block 124, an inner surface of the housing is roughened to achieve a wettability contact angle of at least 90° with respect to the solution or solvent that is to be contained by the packaging to include the low wettability housing. In one implementation, the inner surface of the housing is roughened to achieve a wettability contact angle of at least 90° with respect to water, such that the inner surface is hydrophobic. In another implementation, the inner surface of the housing is roughened to achieve a wettability contact angle of at least 90° with respect to other solvents such as acetone or ethanol. In some implementations, the inner surface of the housing is roughened to achieve greater wettability contact angles, such as contact angles greater than 110° in even greater than 150° with respect to water, acetone, ethanol or other solvents. In one implementation, the roughening of the interior surface of the wall or walls is produced by etching such interior surfaces, such as with an unpatterned laser, chemical or plasma etching.

Figure 4:
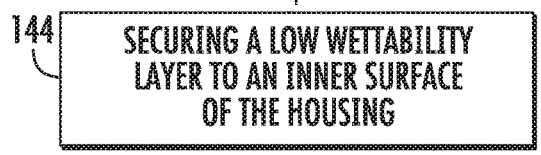
FIG. 4 is a flow diagram of another example method for forming a low wetting package housing.

FIG. 4 is a flow diagram of an example method 140 for forming a low wettability housing for use in method 100 or for use as part of package 20 described above. As indicated by block 142, a housing shaped and sized to form a chamber about an SEL structure on a substrate is formed. In one implementation, the housing may be formed using plating, molding or other fabrication technologies.

As indicated by block 144, a low wettability layer is secured to the inner surface of the housing, such as housing 34, wherein the low wettability layer has a wettability contact angle of at least 90° with respect to the solution or solvent that is to be contained by the packaging to include the low wettability housing. In one implementation, the layer itself may be roughened (as described above) prior to or after being joined to existing wall of the housing, such as housing 34. In one implementation, a layer of material may be coated or otherwise deposited upon the existing wall of housing 34, wherein the material composition of the coating has a low wettability or wettability contact angle of at least 90° as measured with water, acetone or ethanol. In some implementations, a coating of a flourocarbon, such as polytetrafluoroethylene, may be applied to the existing wall of the low wetting housing, wherein the material of the low wetting surface exhibits a wettability contact angle greater than 90° with respect to solvents such as water, acetone or ethanol. In other implementations, the low wettability layer may be formed upon the wall using sole-gel deposition or chemical vapor deposition for growth of nano wires.

Figure 5:
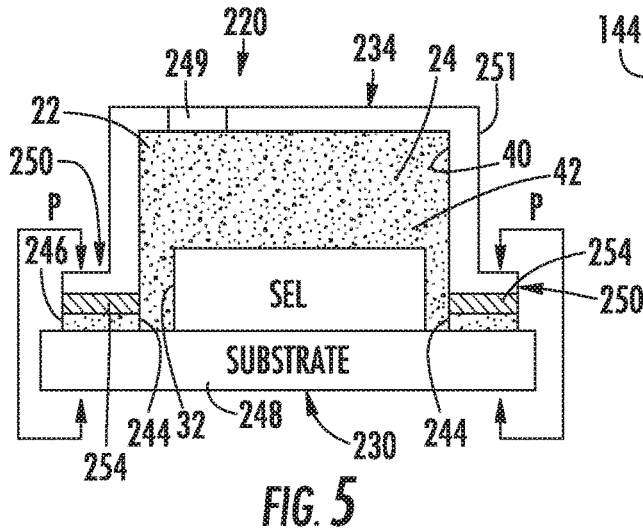
FIG. 5 is a sectional view schematically illustrating another example analyte detection package

FIG. 5 schematically illustrates an example analyte detection package 220. Analyte detection package 220 comprises substrate 230, SEL structure 32 (described above) and housing 234. Substrate 230 cooperates with housing 234 to form an enclosure or chamber 240 that extends about SEL structure 32 and which is to contain solution 22 when being used to test or identify analytes 24 initially provided by solution 22. Substrate 230 comprises a base or platform supporting SEL structure 232. Substrate 230 comprises a surface portion 244 (schematically shown) that is formed from a high surface diffusivity metal. High surface diffusivity metals are metals that may be welded to one another through cold welding or contact welding, a solid-state welding process without fusion or heating at the interface of the two parts being welded. In such cold welding or contact welding processes, the joint does not undergo any liquid or molten phase. Examples of high surface diffusivity metals include, but are not limited to, gold, silver and palladium.

In one implementation, surface portion 244 comprises a pad 246 of high surface diffusivity metal that is secured to or upon a base or foundation portion 248 of substrate 230, wherein substrate 230 is formed from a nonmetal, such as silicon. In another implementation, surface portion 244 comprises a layer of high surface diffusivity metal that is coated, plated, evaporated or otherwise deposited upon portion 248 of substrate 230, wherein substrate 230 is formed from a nonmetal such as silicon. In yet other implementations, foundation portion 248 of substrate 230 may additionally be formed from a metal. In some implementations, the entirety of substrate 238 formed from a high surface diffusivity metal. Although surface portion 244 is illustrated as extending about SEL structure 32, just those regions where housing 234 extends from substrate 230, in other implementations, surface portion 244 may extend across substrate 230, across and below portions of interior 42 of chamber 40. In some implementations, surface portion 244 may extend completely across and below interior 42 and below SEL structure 32. For ease of illustration, the proportional thickness of surface portion 244 is exaggerated.

Housing 234, sometimes referred to as an orifice plate, cooperates with substrate 230 to form and define the interior 42 of chamber 40. Housing 234 protects SEL structure 32 from exposure to the environment and reduces or prevents oxidation of surfaces of SEL structure 32 prior to use. Housing 234 may additionally reduce or prevent unintentional or premature exposure of SEL structure 32 to extraneous substances or an analyte that SEL structure 32 is intended to detect. Although housing 234 and substrate 230 are illustrated as forming a rectangular shaped interior 42, in other implementations, chamber 40 may have other shapes. Although housing 234 is illustrated in FIG. 5 as not having low wettability surface 50 described above with respect to package 20, in other implementations, housing 234 may additionally include low wettability surface 50.

Housing 34 comprises fill opening 249 and rim 250. Fill opening 44 comprise an opening extending through a wall of housing 34. Fill opening 249 facilitates filling of interior 42 with solution 22 including analyte 24. In one implementation, the fill opening is closed by a removable seal that may be peeled away, punctured or torn to expose the fill opening. In one implementation, the opening is formed by peeling, puncturing or penetrating through a portion of the walls of chamber 40. In one implementation, portions of chamber 40 are formed from material or are dimensioned so as to be torn away or peeled away to form the fill opening. In another implementation, chamber 40 has a portion which is to be punctured. In yet another implementation, chamber 40 comprises a septum through which a needle is used to deposit solution 22 containing analyte 24 into the interior 42 of chamber 40.

Rim 250 comprises those portions of housing 234 which are joined to substrate 230. Rim 250 is contact welded or cold welded to opposite surface portions 244 of substrate 230. In the example illustrated, rim 250 comprises outwardly extending lips, rims or flanges projecting outward of the vertical wall portions of housing 234 to provide a greater surface area for cold welding or contact welding with surface portions 244 of substrate 230. In one implementation, rim 250 has an outwardly extending width of at least 2 mm which projects from the vertical walls 251 of housing 234 completely about interior 42. In other implementations, rim 250 may have other sizes and shapes.

As shown by FIG. 5, rim 250 comprises surface portions 254 of high surface diffusivity metal. Surface portion 254 comprises metal surfaces that are cold welded or contact welded with surface portions 244 of substrate 230. The high surface diffusivity metals facilitate cold welding or contact welding of such first and second surface portions 244, 254. Examples of high surface diffusivity metals for surface portions 254 include, but are not limited to, gold, silver and palladium. In one implementation, both of surface portions 244 and 254 comprise gold. In another implementation, both of surface portions 244 and 254 comprise silver. In another implementation, both of surface portions 244 and 254 comprise palladium. In yet other implementations, one of surface portions 244, 254 may comprise one of gold, silver and palladium while the other of surface portions 244, 254 comprises a different one of gold, silver and palladium.

In one implementation, surface portion 254 comprises a pad of a high surface diffusivity metal secured otherwise joined to rim 250. In another implementation, surface portion 254 comprises a coating of high surface diffusivity metal on a lower surface of rim 250. In one implementation, the high surface diffusivity metal is deposited onto rim 250 by the high surface diffusivity metal being evaporated onto the surface of rim 250.

Figure 6:
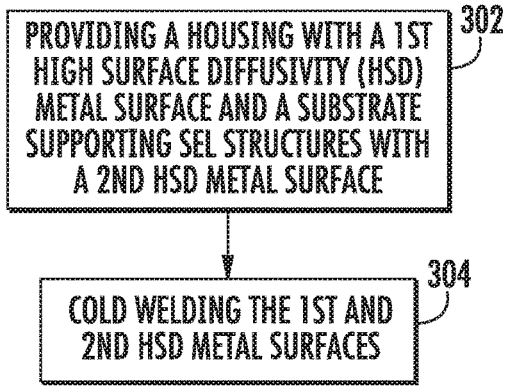
FIG. 6 is a flow diagram of an example method for joining a housing to a substrate supporting SEL structures.

FIG. 6 is a flow diagram of an example method 300 for forming analyte detection package 220. As indicated by block 302, a housing having a first high surface diffusivity metal surface (such as housing 234 with surface portion 254) is provided along with a substrate that supports SEL structures and that has a second high surface diffusivity metal surface (such a substrate 230 with surface portions 244). As indicated by block 304, the first and second high surface diffusivity metal surfaces are cold welded or contact welded to one another to secure the housing to the substrate. Such cold welding or contact welding is performed without the joint undergoing any liquid or molten phase. Such cold welding or contact welding is performed by bringing the two contact surfaces into intimate contact with one another under relatively low-pressure and a relatively low temperatures. In one implementation, such cold welding is performed through the application of pressure P (shown in FIG. 5) of less than or equal to 150 psi (1.034 Mpa). Such cold welding occurs at temperatures less than the melting temperatures of the metals of either of surface portions 244, 254. In one implementation, such cold welding is carried out at room temperature.

Because housing 234 is contact welded or cold welded to substrate 230, the use of adhesives or epoxies to join the housing 234 to the substrate 230 may be reduced or eliminated, reducing risk of subsequent false chemical signals due to outgassing of the epoxy or adhesive and deposition upon SEL structure 32. Because housing 234 is contact welded or cold welded to substrate 230, such welding may occur at low temperatures which may be more compatible with polymeric materials, facilitating the use of polymeric materials for the foundation portion 248 of substrate 230 or for the nonmetal portions of housing 34. Such low temperature bonding may facilitate large volume production use of roll-to-roll imprinting and flexible substrates. The use of high diffusivity metals, such as gold, silver and palladium, in place of epoxies or adhesives, additionally may reduce chemical reaction and contamination concerns.

Figure 7:
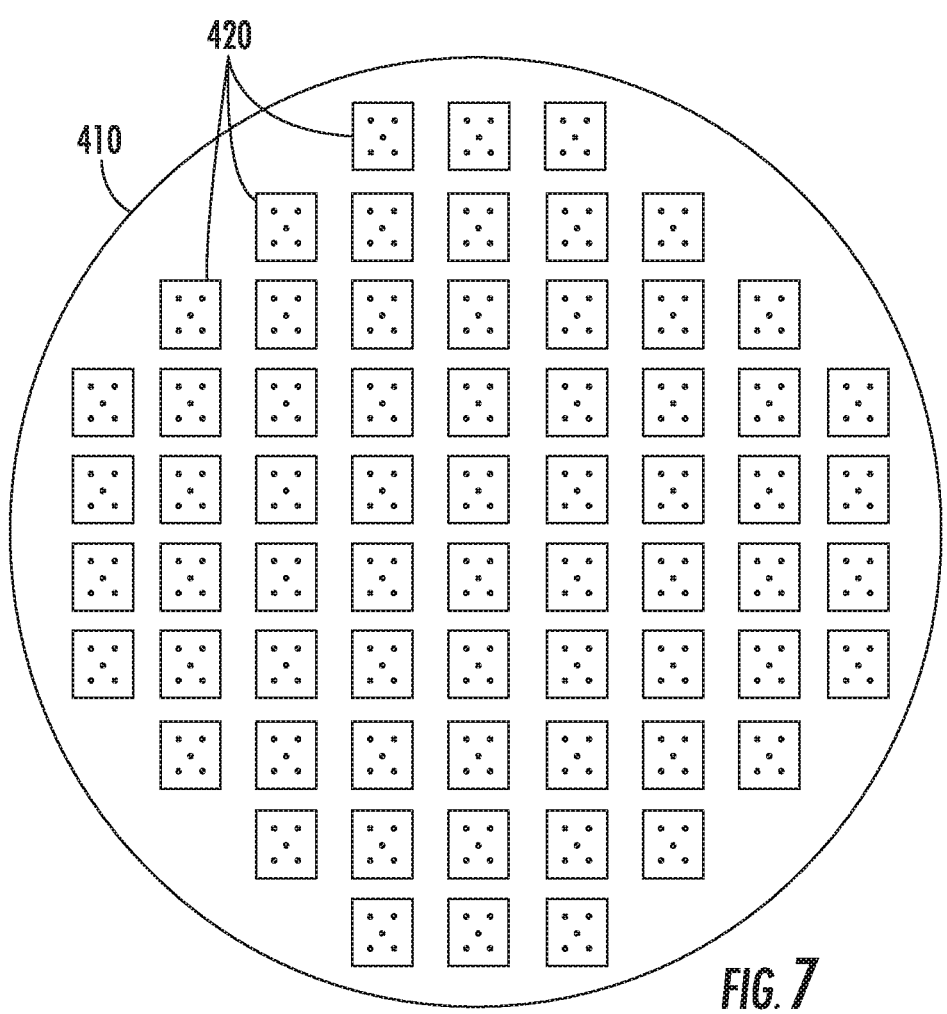
FIG. 7 is a top view of an example wafer including an array of example analyte detection packages.
Figure 8:
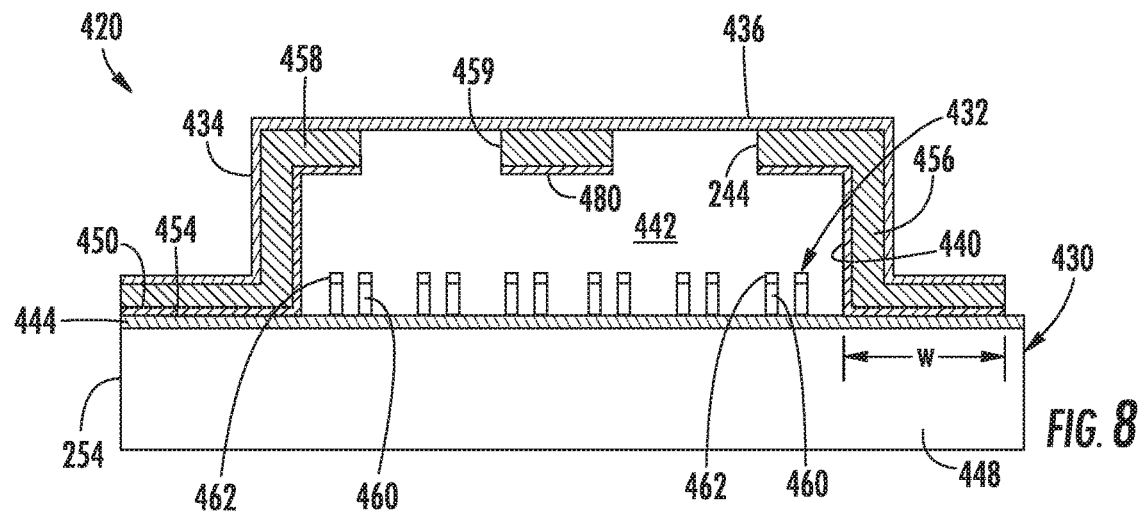
FIG. 8 is a sectional view illustrating an example analyte detection package of the wafer of FIG. 7.

FIGS. 7 and 8 illustrate multiple SEL packages 420, example implementations of packages 20 and 220. As shown by FIG. 7, packages 420 may be formed using semiconductor integrated circuit fabrication techniques as part of a wafer 410. The individual packages 420, formed as part of the wafer 410, are then subsequently separated into individual packages or individual sets of packages.

FIG. 8 is a sectional view illustrating one of packages 420 formed as part of wafer 410. Package 420 comprises substrate 430, SEL structures 432, housing 434 and seal 436. Substrate 432 provides a foundation or platform for housing 434. Substrate 430 cooperates with housing row 434 to form a chamber 440 having an interior 442. Substrate 432 comprises foundation portion 448 and high diffusivity metal surface portion 454. Foundation portion 448 may comprise a metal or nonmetal. High diffusivity metal surface portion 454 comprises a panel or layer of high surface diffusivity metal, such as a high diffusivity metal selected from a group of high diffusivity metals consisting of gold, silver and palladium. In the example illustrated, surface portion 454 extends completely across and below interior 442 as well as below opposing portions of housing 434.

SEL structure 432 comprises columnar supports, pillars, needles, particles, wires or fingers 460. In the example illustrated, each of the fingers 460 comprises a metal cap or head 462 upon which analyte may be deposited. In some implementations, such fingers 460 are formed from materials and/or are dimensioned so as to bend or flex towards and away from one another in response to applied electric fields or in response to micro-capillary forces so as to self-organize, wherein such bending may facilitate close spacing between the structures for greater scattered radiation intensity. In one implementation, the fingers 460 have a nanometer scale to facilitate nano-enhanced Raman spectroscopy (NERS). Such nano-scale NERS structures may increase the intensity of radiation scattered by the analyte absorbed on such structures by a factor as high as $10^{16}$.

In other implementations, SEL structures 432 may comprise other SEL structures such as enhanced fluorescence spectroscopy structures or other enhanced luminescence spectroscopy structures. In yet other implementations, SEL structure 432 may comprise particles, such as nanoparticles, that interact with the deposited analyte so as to enhance the intensity of the radiation scattered by the analyte.

Housing 434 cooperates with substrate 430 to form and define the interior 442 of chamber 440. Housing 434 protects SEL structure 432 from exposure to the environment and reduces or prevents oxidation of surfaces of SEL structure 432 prior to use. Housing 434 may additionally reduce or prevent unintentional or premature exposure of SEL structure 432 to extraneous substances or an analyte that SEL structure 432 is intended to detect. Although housing 434 and substrate 430 are illustrated as forming a rectangular shaped interior 442, in other implementations, chamber 440 may have other shapes.

Housing 434 comprises rim 450, vertical wall portions 456, upper ceiling portion 458 and fill openings 459. Rim 450 comprises those portions of housing 434 that project outwardly from vertical wall portions 456. In one implementation, rim 450 comprises an outwardly extending lip or flange that continuously extends about an entire lower perimeter of package 420 where package 420 joins with substrate 430. Rim 450 provides an enlarged surface area for being cold welded to substrate 430. In one implementation, rim 450 has a width W at least 2 mm.

Rim 450 comprises high surface diffusivity metal surface portions 454. High surface diffusivity metal portions 454 comprise surfaces along the underside of rim 450 including a high surface diffusivity metal such as gold, silver or palladium. High surface diffusivity metal surface portions 454 are contact welded or cold welded to high surface diffusivity metal surface portions 444 of substrate 230. Such contact welding or cold welding may be performed according to block 304 of method 300 shown and described above with respect to FIG. 6.

Vertical wall portions 456 extend from rim 450 and rise above SEL structures 432 to form a dome over and about SEL structures 432. Ceiling portions 458 extends from vertical wall portion 556 over and above SEL structures 432. In the example illustrated, fill openings 459 extend through ceiling portions 458.

In the example illustrated, vertical wall portions 456 and ceiling wall portions 458 include an inner low wetting surface 480. Low wetting surface 480 is similar to low wetting surface 50 described above. In one implementation, low wetting surface 480 has a wettability contact angle of greater than 90° as measured with ethanol. In one implementation, low wetting surface 480 has a wettability contact angle of greater than 110° as measured with ethanol. In yet another implementation, low wetting surface 480 has a wettability contact angle of greater than 150° as measured with ethanol. In other implementations, low wetting surface 480 has a wettability contact angle of at least 90°, nominally greater than 110° or even greater than 150° as measured with other solvents of solution including analyte, such as acetone or water. When measured with water the low wettability nature of surface 480 may be described as hydrophobic.

Because low wetting surface 480 has a wettability contact angle of greater than 90°, as a solution is evaporated, the remaining solution and analyte are less likely to adsorb along the low wetting surface 480, instead subsequently adsorbing onto SEL structure 432. In other words, the liquid or solution will preferentially concentrate away from the interior low wetting surface 480 of housing 434 and therefore on the surface of SEL structure 432 as it dries. The greater concentrations of analyte subsequently adsorbed onto SEL structures 432 may lead to a greater interaction of such analyte molecules with SEL structure 432 to increase sensitivity of sensing carried out utilizing package 420.

In one implementation, low wetting surface 480 is formed by engineering an internal surface of the wall portions 456, 458 forming housing 434. For example, in one implementation, the internal surface of walls 456, 458 forming housing 434 may be roughened so as to achieve the above-described wettability contact angles. In one implementation, interior surface of housing 434 is roughened to a micro roughness of at least one micrometer and up to 100 µm. In another implementation, the micro roughness surface of housing 434 is further roughened to provide a secondary nanoscale roughness of at least 50 nm and up to 200 nm. In essence, the peaks and valleys of the nanoscale roughness areas extend along the peaks and valleys of the micro scale roughness areas. In one implementation, the roughening of the interior surface of the wall or walls of housing 434 to form low wetting surface 480 is produced by etching such interior surfaces, such as with a patterned laser, chemical or plasma etching. In other implementations, such roughening may be induced or carried out by photolithography, imprint lithography been performed on the wall of housing 434.

In other implementations, low wetting surface 480 may be provided on the inner surface of housing 434 by securing a low wettability layer to the inner surface of housing 434. For example, the low wettability layer may be bonded, coated, fused, fastened otherwise joined to the existing walls of housing 434. The low wettability layer that is secured to housing 434 may have a low wettability that is less than the wettability of SEL structure 432 or that has a wettability contact angle of at least 90° as measured with water due to the layer itself being roughened (as described above) or due to the material composition of the layer. For example, in one implementation, low wetting surface 450 may comprise a coating of a material having low wettability or wettability contact angle of at least 90° as measured with ethanol. In one implementation, low wetting surface 480 may comprise a coating of a fluorocarbon, such as polytetrafluoroethylene, wherein the low wetting surface exhibits a wettability contact angle greater than 90° with respect to solvents such as acetone and water. In other implementations, the low wettability layer may be formed upon the wall using sole-gel deposition or chemical vapor deposition for growth of nano wires.

Seal 436 comprises a panel or layer of material coupled to a remainder of package 420 across fill opening 459. Seal 436 provides a hermetic seal to inhibit contamination of interior 442. Seal 436 inhibits oxidation of the metal surfaces within interior 442 prior to use of package 420. Seal 436 further indicates previous use of package 420. Seal 436 may be formed from a polymer tape, plastic, transparent material, plastic sheeting, foil material, foil sheeting, film, membrane, wax or polydimethylsiloxane.

When analyte containing solution is to be deposited within interior 442, seal 446 may be altered to provide access through fill opening 59. In one implementation, seal 436 is releasably or removably adhered to housing 434 by pressure sensitive adhesive or the like that allows seal 436 to be peeled away from fill opening 459. In yet another implementation, seal 436 is formed from a material and/or is dimensioned so as to be punctured through fill opening 244 and/or torn away from opening 459. In yet other implementations, seal 436 comprises a septum that allows insertion of a needle through opening 459, wherein the septum resiliently closes upon withdrawal of the needle. In yet other implementations, seal 436 is provided by a lid, top, door, hatch or cap that temporarily seals or closes opening 459. In some implementations, seal 436 is omitted.

Figure 9:
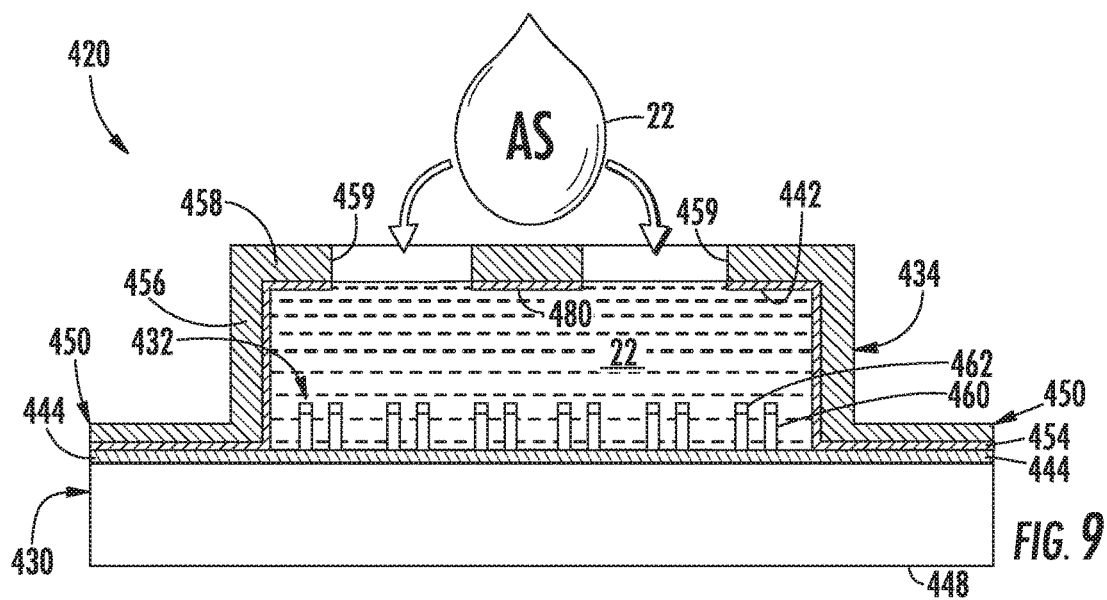
FIG. 9 is a sectional view of the analyte detection package of FIG. 8 illustrating filling of the analyte detection package within analyte containing solution in one example.
Figure 10:
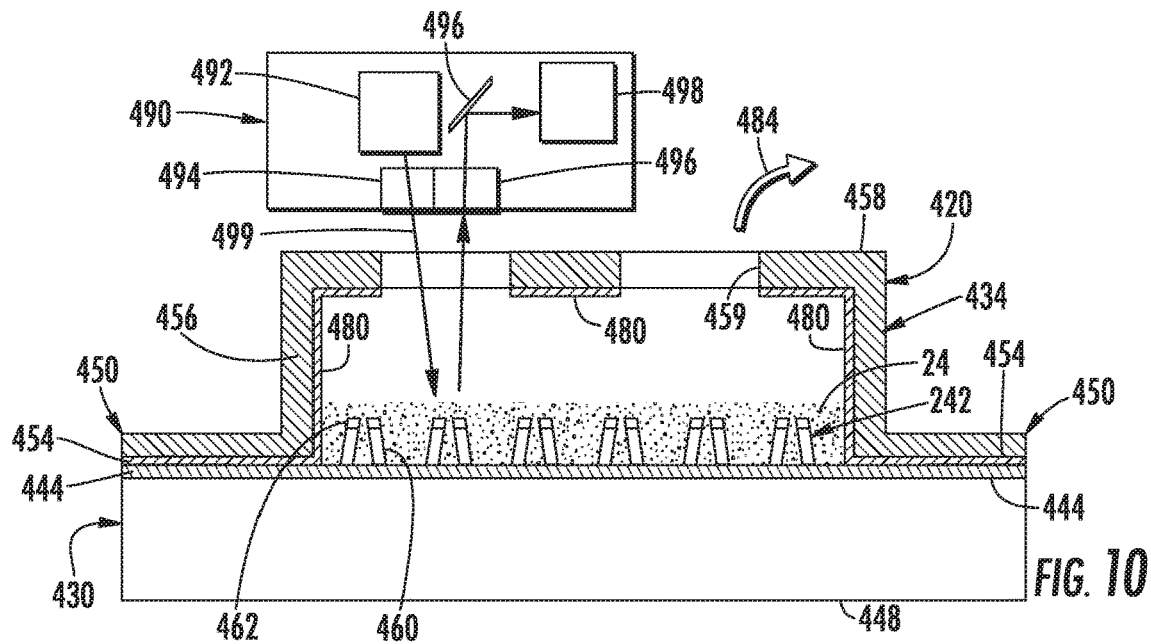
FIG. 10 is a sectional view of the analyte solution within analyte detection package of FIG. 8 being sensed in one example.

FIGS. 9 and 10 illustrate use of package 420 in one example. As shown by FIG. 9, after seal 436 has been peeled away from housing 434, analyte containing solution 22 is deposited into interior 442 through fill opening 459.

As indicated by FIG. 8, the solution 22 is dried or is allowed to dry or evaporate as indicated by arrow 484. As a solution 22 evaporates, solution withdraws from low wetting surface 480 due to the low wettability characteristics of low wettability surface 480. As a result, the analyte 24 is less likely to be adsorbed along low wetting surface 480 and is more likely to concentrate adjacent or upon SEL structures 432.

As further indicated by FIG. 10, packaging 420 is presented to a detector or reader 490 which comprises a radiation emitter 492, focusing optics 494, receiving optics 496 and detector 498. Radiation emitter 492 emits photons 499 which are directed by optics 494 onto SEL structures 432 and analyte 24. In one implementation, radiation emitter 282 comprises a laser, wherein optics 494 comprises a convex lens or other optical devices that impinge SEL structures 432 with a columnar laser beam. Photons 499 are scattered by analyte 24, wherein the intensity of the scattered photons or radiation is enhanced by stage SEL structures 432. The scattered photons 499 return to reader 490, where optics 496, in the form of a lens and/or mirror arrangement direct photons 499 to a detector for 98 which output signals based upon the detected photons 499. A processor, following instructions in a non-transitory computer-readable medium, receives the signals and analyzes the signals to identify or determine characteristics of analyte 24.

FIGS. 11-18 illustrate one example method for forming an analyte detection package housing, such as housing 434. As illustrated by FIG. 11, a photoresist 510 is deposited upon a mandrel 512 and is patterned to form a photoresist mask 514. Mandrel 512 may comprise glass, soda-lime-silica glass of the like.

FIG. 13 illustrates mandrel 512 after wet etching with an etchant such as hydrogen fluoride and after photoresist mask 514 has been removed. As shown by FIG. 13, following such etching, mandrel 512 comprises elongated trapezoidal and/ or conical structures 518 which were previously beneath the photoresist mask 514. As shown by FIG. 14, a physical vapor deposition process is performed to add or sputter a layer 520 of a metal, such as stainless steel and/or chromium to form a mandrel mask on mandrel 512.

As illustrated by FIG. 15, plasma-enhanced chemical vapor deposition and photolithography processes are carried out. The plasma enhanced chemical vapor deposition process deposits a layer of silicon carbide on layer 520. This layer may be subsequently patterned by photolithography to form the silicon carbide structures 524. Silicon carbide structures 524 define corresponding apertures or fill openings 459 of the final housing 434.

In one implementation, as illustrated by FIG. 16, mandrel 512 is immersed in a nickel bath that plates layer 520 nickel layer 528 everywhere except where the nonconductive silicon carbide structures 524 are located. The nickel layer 528 from the bath defines the patterns, shapes and/or features of housing 434.

As illustrated by FIG. 17, etching is carried out upon surface 530 of layer 528 to introduce micro-roughness. In one implementation, the micro-roughness is a micro-roughness of at least one micrometer and up to 100 μm. The micro-roughness provides a low wetting surface (such as low wetting surface 480) having a wettability contact angle of at least 90° when measured with respect to water. In another implementation, the micro-roughness provides the low wetting surface with a wettability contact angle of at least 90° when measured with respect to other solvent such as acetone or ethanol. In yet other implementations, the wettability contact angle provided by the micro-roughness is at least 110° or greater than 150° when measured with respect to water or when measured with respect to acetone or ethanol.

As further illustrated by FIG. 17, a high surface diffusivity metal, such as gold, is evaporated onto the electroplated and etched layer of nickel 528. The high surface diffusivity metal forms a cold welding or contact welding surface to facilitate cold welding or contact welding of the housing with corresponding welding or contact welding surfaces of a substrate, such as substrate 430 described above. Because evaporated metal is naturally rough due to grain structure during such deposition, the evaporated high diffusivity metal enhances metal to metal cold welding or contact welding. As illustrated by FIG. 18, the layer of nickel 528 with its etched surface 530, upon which the metal 532 is evaporated, is peeled away or otherwise removed from mandrel 512 for being contact welded to a substrate supporting an SEL structure. Mandrel 512 with the layer 520 and silicon carbide structures 524 serve as a master for the formation of additional housings 534 following the processes outlined with respect to FIGS. 16-8. In other implementations, housing 534 may be formed using other processes and may be formed using other materials.

Although the present disclosure has been described with reference to example implementations, workers skilled in the art will recognize that changes may be made in form and detail without departing from the spirit and scope of the claimed subject matter. For example, although different example implementations may have been described as including one or more features providing one or more benefits, it is contemplated that the described features may be interchanged with one another or alternatively be combined with one another in the described example implementations or in other alternative implementations. Because the technology of the present disclosure is relatively complex, not all changes in the technology are foreseeable. The present disclosure described with reference to the example implementations and set forth in the following claims is manifestly intended to be as broad as possible. For example, unless specifically otherwise noted, the claims reciting a single particular element also encompass a plurality of such particular elements. The terms "first", "second", "third" and so on in the claims merely distinguish different elements and, unless otherwise stated, are not to be specifically associated with a particular order or particular numbering of elements in the disclosure.

What is claimed is:

1. An analyte detection package comprising:
    a substrate;
    a surface-enhanced luminescence (SEL) structure extending from the substrate, the SEL structure having a first wettability for a given liquid;
    a low wettability housing extending from the substrate to form a chamber between the housing of the substrate about the SEL structure to receive an analyte containing solution, the housing having an inner surface adjacent the chamber, the inner surface having a second wettability for the given liquid less than the first wettability.

2. The analyte detection package of claim 1, wherein the inner surface has a wettability contact angle of greater than 90° as measured with ethanol.

3. The analyte detection package of claim 1, wherein the inner surface has a wettability contact angle of at least 110° as measured with ethanol.

4. The analyte detection package of claim 1, wherein the inner surface has a wettability contact angle of at least 150° as measured with ethanol.

5. The analyte detection package of claim 1, wherein the inner surface has a roughness of between 1 micrometer and 100 μm.

6. The analyte detection package of claim 1, wherein the inner surface has a secondary roughness of between 50 nanometers and 200 nm.

7. The analyte detection package of claim 1, wherein the substrate has a first surface portion formed from a high surface diffusivity metal selected from a group of metals consisting of gold, silver and palladium, wherein the housing has a second surface portion formed from a high surface diffusivity metal selected from a group of metals consisting of gold, silver and palladium and wherein the first surface portion and the second surface portion are contact welded to secure the housing to the substrate.

8. The analyte detection package of claim 1, wherein the inner surface comprises a layer of polytetrafluoroethylene.

9. A method comprising:
    securing a low wettability package housing to a substrate supporting surface enhanced luminescence (SEL) structures, the low wettability package housing being secured over the surface enhanced luminescence structures to form a chamber to contain an analyte containing solution about the SEL structures, the housing having an inner surface having a wettability contact angle of at least 90° as measured with ethanol.

10. The method of claim 9, wherein the inner surface of the housing as a wettability contact angle of at least 90° as measured with ethanol.

11. The method of claim 9 further comprising roughening the inner surface of the housing to a micro roughness of between 1 and 100 μm.

12. The method of claim 9 further comprising bonding the housing to the substrate by pressing the housing and the substrates together with a pressure of less than or equal to 150 psi pressure at room temperature.

13. The method of claim 9, wherein the substrate has a first surface portion, wherein the housing has a second surface portion and wherein securing the housing to the substrate comprises cold welding the first surface portion and the second surface portion.

14. A housing for use with a substrate supporting a surface enhanced luminescence structure to form an analyte detection package, the housing comprising:
   a rim to be secured to the substrate; and
   a dome portion extending from the rim, the rim having a lower surface portion to face the substrate, the lower surface portion formed from a metal selected from a group of metals consisting of gold, silver and palladium.

15. The housing of claim 14, wherein the dome portion has an inner surface having a wettability contact angle of at least 90° as measured with ethanol.

* * * * *